United States Patent [19]
Thigpen

[11] Patent Number: 5,695,615
[45] Date of Patent: *Dec. 9, 1997

[54] PURIFICATION PROCESS FOR CYCLIC FORMULAS

[75] Inventor: Hubert H. Thigpen, Corpus Christi, Tex.

[73] Assignee: Hoechst Celanese Corporation, Warren, N.J.

[ * ] Notice: The term of this patent shall not extend beyond the expiration date of Pat. No. 5,690,793.

[21] Appl. No.: 510,047

[22] Filed: Aug. 1, 1995

Related U.S. Application Data

[63] Continuation of Ser. No. 180,013, Jan. 11, 1994, abandoned.
[51] Int. Cl.⁶ .................... B01D 3/34; C07D 317/12
[52] U.S. Cl. .................... 203/17; 203/63; 203/64; 203/74; 203/81; 549/430
[58] Field of Search .................... 203/14, 17, 64, 203/63, 74, 81; 549/430, 377; 210/664, 694

[56] References Cited

U.S. PATENT DOCUMENTS

| | | | |
|---|---|---|---|
| 2,350,940 | 6/1944 | Squires | 549/430 |
| 3,857,759 | 12/1974 | Fiore et al. | 203/14 |
| 4,007,095 | 2/1977 | Wolf et al. | 203/64 |
| 4,229,262 | 10/1980 | Reed et al. | 203/64 |
| 4,764,626 | 8/1988 | Heuvelsland | 549/377 |
| 5,616,736 | 4/1997 | Thigpen | 549/430 |

OTHER PUBLICATIONS

CA 118: 126957 Abstract.

*Primary Examiner*—Virginia Manoharan
*Attorney, Agent, or Firm*—James M. Hunter, Jr.

[57] ABSTRACT

A purification process for cyclic formals, in which water is efficiently removed from a crude cyclic formal, namely, a mixture of a cyclic formal and water which is difficult to be separated from the mixture, thereby obtaining a cyclic formal of high purity which contains only a very small amount of water.

The purification process for cyclic formals is characterized by the following two purification steps:

(1) Supplying a mixture of a cyclic formal and water into a distillation tower at a supply position, and effecting distillation while supplying a hydrophilic solvent (A) having a boiling point from 180° to 250° C. at a position higher than the supply position of the mixture to take out a cyclic formal (X) containing 100 to 5000 ppm of water as a distillate, and (2) Distilling the cyclic formal (X) obtained in step (1) or treating it with a dehydrant to obtain a purified cyclic formal (Y) which contains less water than in the cyclic formal (X).

8 Claims, 2 Drawing Sheets

PURIFICATION PROCESS FOR CYCLIC FORMULAS

This is a continuation of application Ser. No. 08/180,013 filed on Jan. 11, 1994, now abandoned.

BACKGROUND OF THE INVENTION

1. Field of the Invention

The present invention relates to a purification process for cyclic formals which are useful as solvents, intermediates of drugs, starting materials for resins, and the like. More particularly, it relates to an economically advantageous purification process for obtaining cyclic formals of high purity which contains only a very small amount of water, in which water is efficiently removed from a mixture of a cyclic formal and water which is difficult to be separated from the mixture because of the azeotropy between cyclic formal and water.

2. Description of Related Art

Cyclic formals typified by 1,3-dioxolan, 1,4-butanediol formal, diethylene glycol formal, 4-methyl-1,3-dioxolan, 1,3-dioxane, 1,3,6-trioxolane, etc. are known to be obtainable from cyclizing reactions between a corresponding glycol and an aldehyde, and between a corresponding alkylene oxide and an aldehyde. For example, concerning a method for preparing a typical cyclic formal, 1,3-dioxolan, German patent No. 1914209 discloses a process for preparing it by reacting glycol with formaldehyde in the presence of an acid catalyst, and Ind. Eng. Chem., 46,787 (1954) and U.S. Pat. No. 3,857,759 both disclose a process for preparing 1,3-dioxolan by reacting glycol and paraformaldehyde in the presence of an acid catalyst.

These processes for preparing cyclic formals which employ a glycol and an aldehyde as starting materials involve drawbacks in that the cyclic formal produced and a by-produced water or water which is present in a form of an aqueous aldehyde solution often co-boil (azeotropy), thereby rendering separation of water difficult by ordinary distillation steps.

Taking 1,3-dioxolan as an example, the above mentioned German patent No. 1914209 describes that as much as 7% of water is contained. In order to obtain 1,3-dioxolan of high purity by removing water from a mixture of 1,3-dioxolan and water, the above-mentioned Ind. Eng. Chem., 46,787 (1954) discloses a process in which a reaction distillate containing 1,3-dioxolan and water is added with sodium chloride for phase separation into two phases, and the organic phase is subjected to a further distillation for purification, while U.S. Pat. No. 3,857,759 discloses a process in which a reaction distillate is added with cyclohexane before purification. However, the former is not suitable as an industrial purification process, and the latter raises a problem in that water cannot be separated sufficiently for obtaining 1,3-dioxolan of high purity.

These phenomena do not specifically occur only in processes for preparing 1,3-dioxolan, but are common in processes for obtaining cyclic formals which form an azeotropic system with water. Accordingly, an economical purification process for obtaining cyclic formals of high purity in which water is efficiently removed from a mixture of a cyclic formal and water has still been desired.

Under the above circumstances, the present inventors have carried out extensive studies in order to solve the aforementioned problems. Having combined two purification steps, namely, the first step of extraction distillation and the second step of other purification method, they conducted extensive studies on conditions under which cyclic formals of high purity can be efficiently obtained, leading to completion of the present invention.

SUMMARY OF THE INVENTION

Accordingly, an object of the present invention is to provide a purification process for a cyclic formal which comprises the following purification step (1) and purification step (2):

(1) Supplying a mixture of a cyclic formal and water into a distillation tower at a supply position, and effecting distillation while supplying a hydrophilic solvent (A) having a boiling point from 180° to 250° C. at a position higher than the supply position of the mixture to take out a cyclic formal (X) containing 100 to 5000 ppm of water as a distillate, and (2) Distilating the cyclic formal (X) obtained in step (1) or treating it with a dehydrant to obtain a purified cyclic formal (Y) which contains less water than in the cyclic formal (X).

Another object of the present invention is to provide a purification process for a cyclic formal as described above, wherein the cyclic formal (Y) contains not more than 100 ppm of water.

Another object of the present invention is to provide a purification process for a cyclic formal as described above, wherein the hydrophilic solvent (A) is a polyol, a dimer thereof, or a monoalkylether of a polyol or the dimer.

Another object of the present invention is to provide a purification process for a cyclic formal as described above, wherein the hydrophilic solvent (A) is selected from the group consisting of 1,4-butanediol, diethylene glycol, 1,2-propanediol, 1,3-propanediol, dipropylene glycol and monomethyl ethers thereof.

Another object of the invention is to provide a purification process for a cyclic formal as described above, wherein a pre-concentrated mixture which contains a cyclic formal having a concentration more than 80% by weight up to a concentration which forms an azeotrope is supplied to the tower.

Another object of the invention is to provide a purification process for a cyclic formal as described above, wherein the quantity of the hydrophilic solvent (A) supplied is from 1 to 15 times, on a molar basis, the quantity of water in the mixture of cyclic formal and water.

Another object of the invention is to provide a purification process for a cyclic formal as described above, wherein the cyclic formal is 1,3-dioxolan.

The above and other objects, features and advantages of the present invention will become apparent from the following description.

DETAILED DESCRIPTION OF THE INVENTION AND PREFERRED EMBODIMENTS

The present invention is directed to a purification process of cyclic formals, and specific examples of the cyclic formals to which the present invention is applicable include 1,3-dioxolan, 1,4-butanediol formal, diethylene glycol formal, 4-methyl-1,3-dioxolan and 1,3-dioxane, with 1,3-dioxolan being preferable.

Figure 1:
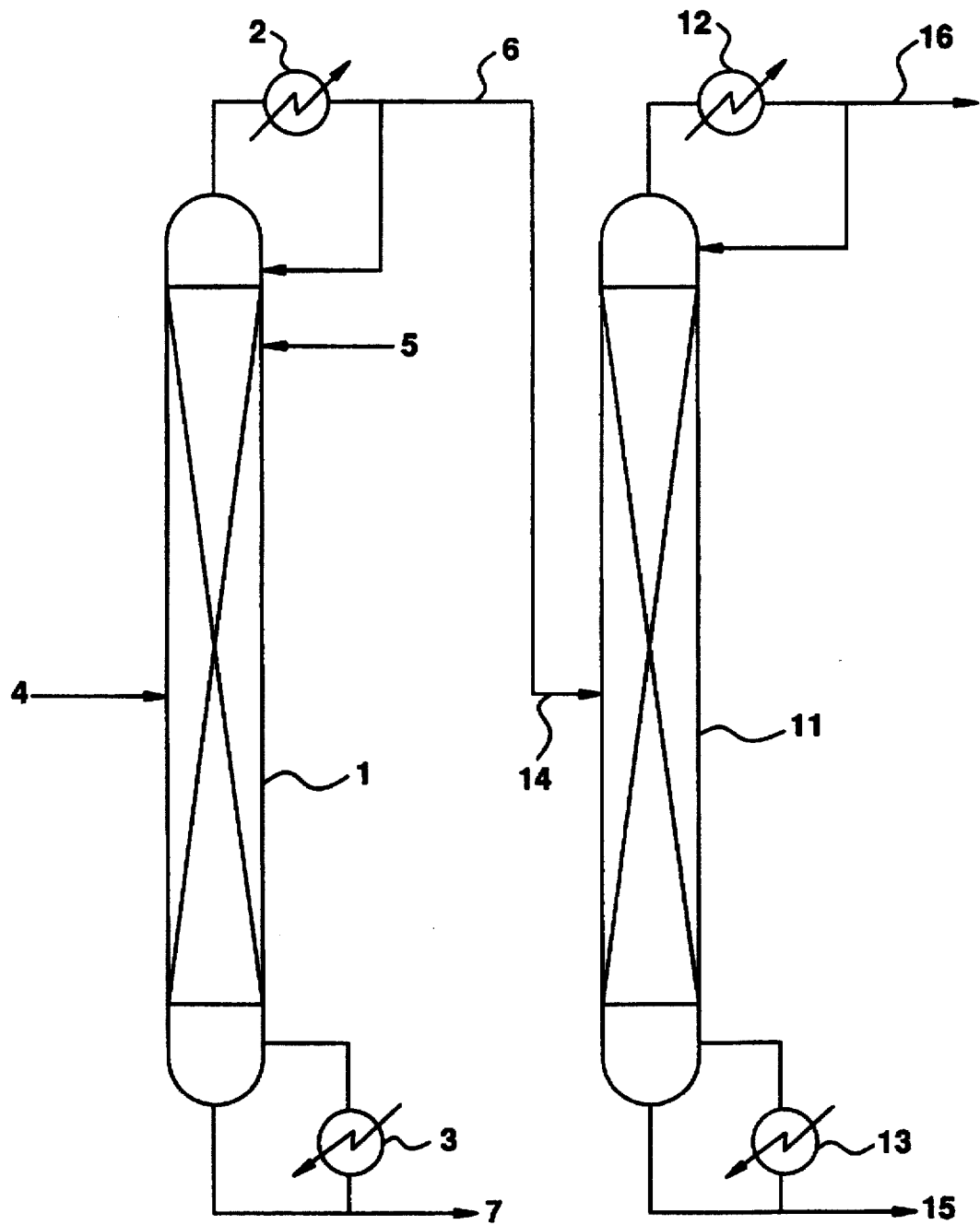
FIG. 1 is a schematic diagram showing the purification process for cyclic formals according to the present invention.

The present invention will now be described with reference to the distillation system shown in FIG. 1. In FIG. 1, numeral 1 indicates a distillation tower to be used in the first purification step, numeral 2 indicates a condenser, numeral 3 indicates a reboiler, numeral 4 indicates a supply position of a mixture containing a cyclic formal and water, numeral 5 indicates a supply position of a hydrophilic solvent (A), numeral 6 indicates a distillate at the top (may be referred to as a top distillate), and numeral 7 indicates a bottom waste. As described hereinbefore, purification of cyclic formals involves a limitation, that is, they cannot be purified beyond the azeotropic composition of a cyclic formal and water by ordinary distillation procedures. However, according to the present invention, supply of a hydrophilic solvent (A) into the distillation tower 1 destroys the azeotropic system formed in ordinary distillations, allowing water and impurities to be removed and yielding a highly purified cyclic formal containing only 100 to 5000 ppm of water as a distillate from the top. Water contained in the starting mixture, part of a cyclic formal, hydrophilic solvent (A), and impurities such as formaldehyde and reaction byproducts are taken out as a waste 7 from the bottom of the tower.

The hydrophilic solvents (A) used in the present invention are preferably those which are miscible with water in arbitrary proportions at ordinary temperatures, and have a boiling point from 180° to 250° C., preferably from 190° to 250° C. Examples of the hydrophilic solvents (A) include polyols, dimers of polyols, and monoalkylethers of polyols and the dimers. Preferable alkyl groups of the monoalkylethers are those having 1 to 4 carbon atoms, among which methyl and ethyl are more preferred, with methyl being particularly preferred. Specific examples of the hydrophilic solvents (A) include 1,4-butanediol, diethylene glycol, 1,2-propanediol, 1,3-propanediol, dipropylene glycol, ethylene glycol and monomethyl ethers thereof. These hydrophilic solvents (A) are used singly or in arbitrary combination of two or more. Among the species of hydrophilic solvents (A), 1,4-butanediol, diethylene glycol, 1,2-propanediol are preferred.

The amount of hydrophilic solvent (A) to supply is not particularly limited. It is generally from 1 to 15 times, particularly preferably from 1.5 to 10 times, in a molar ratio, the quantity of water contained in the mixture of cyclic formal and water.

As described above, when cyclic formals are prepared by a conventional process, they contain a considerable amount of water. Taking 1,3-dioxolan as an example of a cyclic formal, reaction between an aqueous solution containing 50% by weight of formaldehyde and an equimolar amount of ethylene glycol to formaldehyde theoretically yields a mixture of 60.7% by weight of 1,3-dioxolan and 39.3% by weight of water.

In order to further purify cyclic formals containing a considerable amount of water by extraction distillation, a large amount of a hydrophilic solvent (A) is needed. To deal with a lot of hydrophilic solvent (A), the diameter of the distillation tower must be increased and the tower itself must be high. This means increased cost of installation which invites increased cost of the purification. Moreover, in cases where the hydrophilic solvent (A) is recovered from the bottom waste for reuse, considerable amounts of water must be removed therefrom, which requires high energy.

Accordingly, in the practice of the present invention, it is preferred that the mixture to be supplied be properly dehydrated in advance by ordinary distillation procedures or the like so as to raise the concentration of cyclic formal not less than 80% by weight, preferably in the range from 90% by weight to a concentration of the azeotrope.

In the purification process according to the present invention, the position at which the hydrophilic solvent (A) is supplied to the distillation tower 1 is any position higher than the supply position of the mixture of cyclic formal and water. It is preferred that the distance between the two positions be as long as possible. However, in order to prevent hydrophilic solvent (A) from migrating into the top distillate 6 and contaminating it, it is preferable that the supply position is the second plate or a lower plate counted from the top plate, more preferably between the positions of several and about 10 plates lower from the top plate if the distillation tower 1 is a plate distillation tower as described hereinlater. This sufficiently prevents the hydrophilic solvent (A) from migrating into the distillate 6 and contaminating it. The water content in the cyclic formal of distillate 6 can be suppressed at a low level of 100 to 5000 ppm as described before by selecting the supply position of the hydrophilic solvent (A) and controlling the amount of the supply. Similarly, if the distillation tower is a packed distillation tower, the position at which the hydrophilic solvent (A) is supplied is preferably not higher than 0.5 in terms of the theoretical plate number counted from the top of the tower, more preferably several theoretical plates below. In this connection, the supply position of the mixture may be at the positions of plates, packed portion, or bottom of the tower 1 as long as the above conditions are met. Moreover, the top distillate may be refluxed if necessary.

No particular limitation is imposed on the types of distillation tower 1 useful for purifying cyclic formals according to the present invention. In cases where plate distillation towers are used, any known types are usable including bubble cap tray, uniflux tray, bulb tray, Natter bulb tray, ballast tray, sieve tray, Venturi tray, Kittel tray, turbo grid tray, ripple tray and the like.

The distillation tower may be a packed distillation tower. Any types of packing materials are usable including those of ring types such as Raschig rings, Lessing rings, divided rings and pole rings; saddle types such as bar saddles and interlock saddles; and other types such as Goodroigh packings, Stedman packings, Dickson rings, McMahon packings, helix packings, teralet, cross-spiral packings and so on.

According to the purification process of the present invention, it is necessary that the water content of cyclic formal (X) be reduced to fall within the range of 100 to 5000 ppm, preferably 100 to 2000 ppm in the first purification step, Step (1). By this preliminary reduction of the water content in the above ranges, it is possible to easily remove water contained in cyclic formal to a preferable level, namely 100 ppm or less by a further distillation or the like in the second step, Step 2. This two-step purification is accompanied by another advantage in that it is no more necessary to increase the amount of the hydrophilic solvent (A) to be used in Step 1 or to make the distillation tower high. The cyclic formal (X) obtained in Step 1 is further distilled or treated with a dehydrant in Step 2, yielding a very pure cyclic formal containing less amount of water than cyclic formal (X), preferably containing 100 ppm or less water. In FIG. 1, the second purification step (Step 2) is carried out in distillation tower 11. A cyclic formal (X) in which water content has been reduced in the first step (Step 1) is supplied to the distillation tower 11 as a liquid or as vapor at position 14. The distillation tower may be a plate distillation tower or a packed distillation tower similar to the distillation tower 1. In FIG. 1, numeral 12 indicates a condenser and numeral 13 indicates a reboiler. In the distillation tower 11, major part of water contained in cyclic formal (X) supplied at position 14 is taken out as part of a relatively small amount of distillate 16 which also contain a cyclic formal and impurities of low boiling points if cyclic formal (X) contains such impurities. In the meantime, a highly purified cyclic formal (Y) in which water content has been further reduced to be 100 ppm or less, more preferably 50 ppm or less is obtained as a relatively large amount of bottom liquid 15. The water content of the bottom liquid 15 can readily be reduced to 100 ppm or less by selecting the supply position of cyclic formal (X), changing the total number of plates of the tower, and controlling the reflux ratio, etc. Since water is a substance which is difficult to be separated from cyclic formals, considerably great reflux ratio is required in general.

In Step 2, cyclic formal (X) may be treated with dehydrants. The dehydrants must be inert against cyclic formals. Specific examples of such dehydrants include anhydrous sodium sulfate, quick lime, silica gel, molecular sieve, activated carbon and the like. The purification process of the present invention is very useful for purifying 1,3-dioxolan.

EXAMPLES

The present invention will further be described by way of examples, which however, should not be construed as limiting the invention thereto.

Example 1

Figure 2:
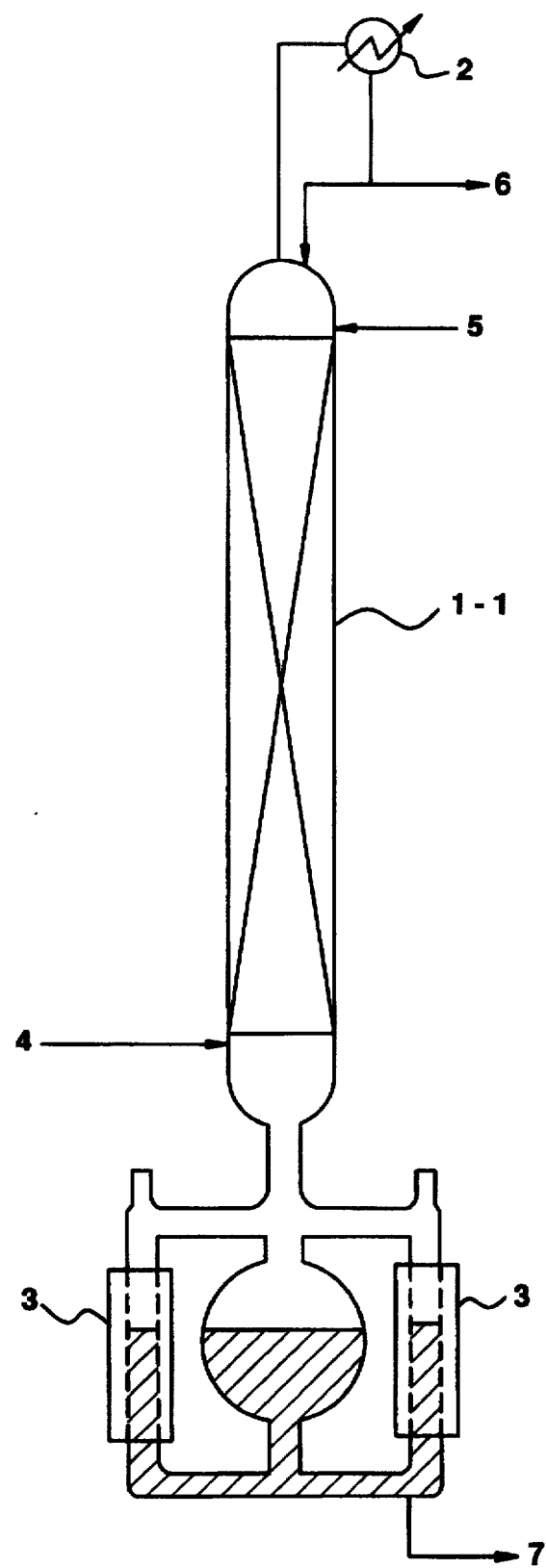
FIG. 2 is a schematic diagram showing the distillation system used in Examples according to the present invention.

Distillation was performed using a distillation system as shown in FIG. 2, where the distillation tower 1-1 was a plate distillation tower (diameter of the tower=50 mm, 45 plates, sieve tray). The distillation tower 1-1 was fed with a mixture containing 91.0% by weight of 1,3-dioxolan, 8.5% by weight of water and 0.5% by weight of impurities (primarily methanol) at the bottom of the tower at a flow rate shown in Table 1, while a hydrophilic solvent (A) shown in Table 1 was fed from the top at the flow rate shown in Table 1. The flow rates of distillate 6 from the top and waste 7 from the bottom under the steady conditions are shown in Table 1. The compositions of the top distillate, and the bottom waste under the steady conditions are shown in Table 2.

TABLE 1

| Hydrophilic solvent (A) | Ex.1 BD | Ex.2 DEG | Ex.3 PD |
|---|---|---|---|
| Flow rate of mixture supplied (g/hr) | 450 | 450 | 450 |
| Flow rate of hydrophilic solvent (A) supplied (g/hr) | 500 | 550 | 600 |
| Flow rate of distillate from the top (g/hr) | 350 | 350 | 350 |
| Flow rate of waste from the bottom (g/hr) | 600 | 650 | 700 |

BD: 1,4-butanediol
DEG: diethylene glycol
PD: 1,2-propanediol

TABLE 2

| Hydrophilic solvent (A) | Ex.1 BD | Ex.2 DEG | Ex.3 PD |
|---|---|---|---|
| Distillate from the top | | | |
| 1,3-Dioxolan (% by weight) | 99.2 | 99.2 | 99.2 |
| Water (ppm) | 720 | 685 | 840 |
| Low boiling point impurities (% by weight) | 0.7 | 0.7 | 0.7 |
| Waste from the bottom | | | |
| 1,3-Dioxolan (% by weight) | 10.5 | 9.7 | 8.8 |
| Water (% by weight) | 6.3 | 5.9 | 5.6 |
| Hydrophilic solvent (A) (% by weight) | 83.2 | 84.4 | 85.6 |

BD: 1,4-butanediol
DEG: diethylene glycol
PD: 1,2-propanediol

The top distillate of the distillation tower 1-1 in Example 1 was supplied to another distillation tower (diameter of the tower=50 mm, 45 plates, sieve tray) at the 30 th plate counted from the bottom at 350 g/hr, and distillation was effected with a reflux ratio 10. The compositions of the top distillate and the bottom liquid under the steady operation (flow rate of the top distillate=20 g/hr, flow rate of the bottom liquid=330 g/hr) were as follows:

| Top distillate: | 1,3-Dioxolan (87.3% by weight), Water (1.2% by weight) Impurities of low boiling point (11.5% by weight) |
|---|---|
| Bottom liquid: | 1,3-Dioxolan (not less than 99.9% by weight), Water (45 ppm) Impurities of low boiling point (not detected). |

As understood from the above data, a very pure 1,3-dioxolan which is almost free of water and impurities having low boiling points was obtained as a bottom liquid. In this connection, the compositions of the top distillates obtained in Examples 2 and 3 were almost the same as in Example 1, therefore, it is readily predicted that the similar results to the above data could be obtained.

Comparative Examples 1 to 3

When distillation was effected only in the distillation tower 1-1, and further purification was not performed by another distillation tower, the water contents of 1,3-dioxolan obtained in these Comparative Examples were 720, 685 and 840 ppm, respectively, and the contents of low boiling point impurities were each 0.7% by weight. Cyclic formals of such poor purification levels are not suitable as starting materials of polymers for polymerization, which requires a very strict purity.

As described hereinabove, the present invention provides an economical purification process for crude cyclic formals containing water which was conventionally thought to be difficult to purify because of the azeotropy between the formals and water. The process of the invention yields highly pure cyclic formals on a steady basis, and is very useful and advantageous in the industry.

I claim:

1. A purification process for removing water from a cyclic formal which comprises the steps of:
   (a) supplying a mixture of a cyclic formal and water into a distillation tower at a supply position, and effecting distillation while supplying a hydrophilic solvent (A) at a position higher than the supply position of the mixture, wherein the hydrophilic solvent (A) is selected from the group consisting of butanediol monomethyl ether, diethylene glycol monomethyl ether, 1,2-propanediol monomethyl ether, 1,3-propanediol monomethyl ether, and dipropylene glycol monomethyl ether, characterized as exhibiting a boiling point from 180° to 250° C., and removing a cyclic formal (X) containing 100 to 5000 ppm of water as a distillate and the hydrophilic solvent (A) and water from the bottom of the tower; and (b) further processing the cyclic formal (X) obtained in step (a) by a process selected from the group consisting of distillation and dehydration with a dehydrant to obtain a cyclic formal (Y) characterized as containing less than about 100 ppm of water.

2. The process according to claim 1, wherein a preconcentrated mixture which contains a cyclic formal having a concentration more than 80% by weight up to a concentration which forms an azeotrope of cyclic formal and water is supplied to the tower.

3. The process according to claim 1, wherein the quantity of the hydrophilic solvent (A) supplied is from 1 to 15 times, on a molar basis, the quantity of water in the mixture of cyclic formal and water supplied to the tower.

4. The process according to claim 1, wherein the cyclic formal is 1,3-dioxolan.

5. A purification process for removing water from a cyclic formal which comprises the steps of:

(a) supplying a mixture of a cyclic formal and water into a distillation tower at a supply position, and effecting distillation while supplying a hydrophilic solvent (A) at a position higher than the supply position of the mixture, wherein the hydrophilic solvent (A) is selected from the group consisting of 1,4-butanediol monomethyl ether, diethylene glycol monomethyl ether, 1,2-propanediol monomethyl ether, 1,3-propanediol monomethyl ether, and dipropylene glycol monomethyl ether, characterized as exhibiting a boiling point from 180° to 250° C., and removing a cyclic formal (X) containing 100 to 5000 ppm of water as a distillate and the hydrophilic solvent (A) and water from the bottom of the tower; and (b) further processing the cyclic formal (X) obtained in step (a) by a process of dehydration with a dehydrant selected from the group consisting of anhydrous sodium sulfate, quick lime, silica gel, molecular sieve, and activated carbon to obtain a cyclic formal (Y), characterized as containing less than about 100 ppm of water.

6. The process according to claim 5, wherein a preconcentrated mixture which contains a cyclic formal having a concentration more than 80% by weight up to a concentration which forms an azeotrope of cyclic formal and water is supplied to the tower.

7. The process according to claim 5 wherein the quantity of the hydrophilic solvent (A) supplied is from 1 to 15 times, on a molar basis, the quantity of water in the mixture of cyclic formal and water supplied to the tower.

8. The process according to claim 5, wherein the cyclic formal is 1,3-dioxolan.

* * * * *